US 6,676,677 B2

(12) United States Patent
Klein

(10) Patent No.: US 6,676,677 B2
(45) Date of Patent: Jan. 13, 2004

(54) LIPOSUCTION CANNULA WITH ABRADING APERTURES

(76) Inventor: Jeffrey A. Klein, 30280 Rancho Viejo Rd., San Juan Capistrano, CA (US) 92675

(*) Notice: Subject to any disclaimer, the term of this patent is extended or adjusted under 35 U.S.C. 154(b) by 221 days.

(21) Appl. No.: 09/853,224

(22) Filed: May 11, 2001

(65) Prior Publication Data

US 2002/0169469 A1 Nov. 14, 2002

(51) Int. Cl.[7] .................. A61B 17/32; A61M 1/00
(52) U.S. Cl. .................. 606/171; 604/22; 604/35
(58) Field of Search .................. 606/167, 170, 606/171, 172, 168, 169; 604/22, 35, 36, 48, 27, 19, 43, 239, 902, 523, 264, 268, 93.01

(56) References Cited

U.S. PATENT DOCUMENTS

| 2,708,437 | A | * | 5/1955 | Hutchins .................. 606/171 |
| 3,082,805 | A | | 3/1963 | Royce |
| 3,732,858 | A | | 5/1973 | Banko |
| 3,734,099 | A | | 5/1973 | Bender et al. |
| 3,955,579 | A | | 5/1976 | Bridgman |
| 3,994,297 | A | | 11/1976 | Kopf |
| 4,167,944 | A | | 9/1979 | Banko |
| 4,203,444 | A | | 5/1980 | Bonnell et al. |
| 4,311,140 | A | | 1/1982 | Bridgman |
| 4,314,560 | A | | 2/1982 | Helfgott et al. |
| 4,487,600 | A | * | 12/1984 | Brownlie et al. .............. 604/35 |
| 4,530,356 | A | | 7/1985 | Helfgott et al. |
| 4,536,180 | A | | 8/1985 | Johnson |
| 4,577,629 | A | | 3/1986 | Martinez |
| 4,589,414 | A | | 5/1986 | Yoshida et al. |
| 4,713,053 | A | | 12/1987 | Lee |
| 4,735,605 | A | | 4/1988 | Swartz |
| 4,775,365 | A | | 10/1988 | Swartz |
| 4,784,649 | A | | 11/1988 | Imonti et al. |
| 4,815,462 | A | | 3/1989 | Clark |
| 4,850,354 | A | | 7/1989 | McGurk et al. |
| 4,886,491 | A | | 12/1989 | Parisi et al. |
| 4,919,129 | A | | 4/1990 | Weber, Jr. et al. |
| 4,925,450 | A | | 5/1990 | Imonti et al. |
| 4,932,935 | A | | 6/1990 | Swartz |
| 4,938,743 | A | | 7/1990 | Lee |
| 5,052,999 | A | | 10/1991 | Klein |
| 5,112,302 | A | | 5/1992 | Cucin |
| 5,181,907 | A | | 1/1993 | Becker |
| 5,236,414 | A | | 8/1993 | Takasu |
| 5,242,386 | A | | 9/1993 | Holzer |
| 5,244,458 | A | | 9/1993 | Takasu |
| 5,286,253 | A | | 2/1994 | Fucci |
| 5,295,980 | A | * | 3/1994 | Ersek .................. 606/171 |
| 5,314,407 | A | | 5/1994 | Auth et al. |
| 5,348,535 | A | | 9/1994 | Cucin |
| 5,352,194 | A | | 10/1994 | Greco |
| 5,489,291 | A | * | 2/1996 | Wiley .................. 606/170 |
| 5,643,198 | A | | 7/1997 | Cucin |
| 5,725,495 | A | * | 3/1998 | Strukel et al. .................. 604/22 |

(List continued on next page.)

Primary Examiner—A. Vanatta
(74) Attorney, Agent, or Firm—Stetina Brunda Garred & Brucker

(57) ABSTRACT

A liposuction cannula with abrading suction apertures and a method of using a cannula with abrading suction apertures are disclosed. The liposuction cannula comprises: a hand-holdable housing having a cavity; a cannular tube having a distal end and a proximal end, the proximal end of the cannular tube being insertable within the cavity; and a plurality of abrading suction apertures about the cannular tube distal end. The abrading suction apertures can be arranged in a variety of configurations, for example, axially about the distal end of the cannular tube, radially about the distal end of the cannular tube or angularly about the distal end of the cannular tube. The abrading suction apertures include a hole, and an abrading member which may be a raised leading edge, a depressed trailing edge, or both a raised leading edge and a depressed trailing edge.

11 Claims, 3 Drawing Sheets

U.S. PATENT DOCUMENTS

| | | |
|---|---|---|
| 5,795,323 A | 8/1998 | Cucin |
| 5,817,050 A | 10/1998 | Klein |
| 5,884,631 A | 3/1999 | Silberg |
| 5,947,988 A * | 9/1999 | Smith .................. 606/167 |
| 5,968,008 A * | 10/1999 | Grams .................. 604/35 |
| 6,020,196 A * | 2/2000 | Hu et al. ................ 604/22 |
| 6,039,048 A | 3/2000 | Silberg |
| 6,102,885 A | 8/2000 | Bass |
| 6,113,569 A | 9/2000 | Becker |
| 6,129,701 A | 10/2000 | Cimino |
| 6,436,116 B1 * | 8/2002 | Spitz et al. ............ 606/170 |
| 6,440,147 B1 * | 8/2002 | Lee et al. ............... 606/170 |
| 2002/0038130 A1 * | 3/2002 | Adams .................. 606/170 |

* cited by examiner

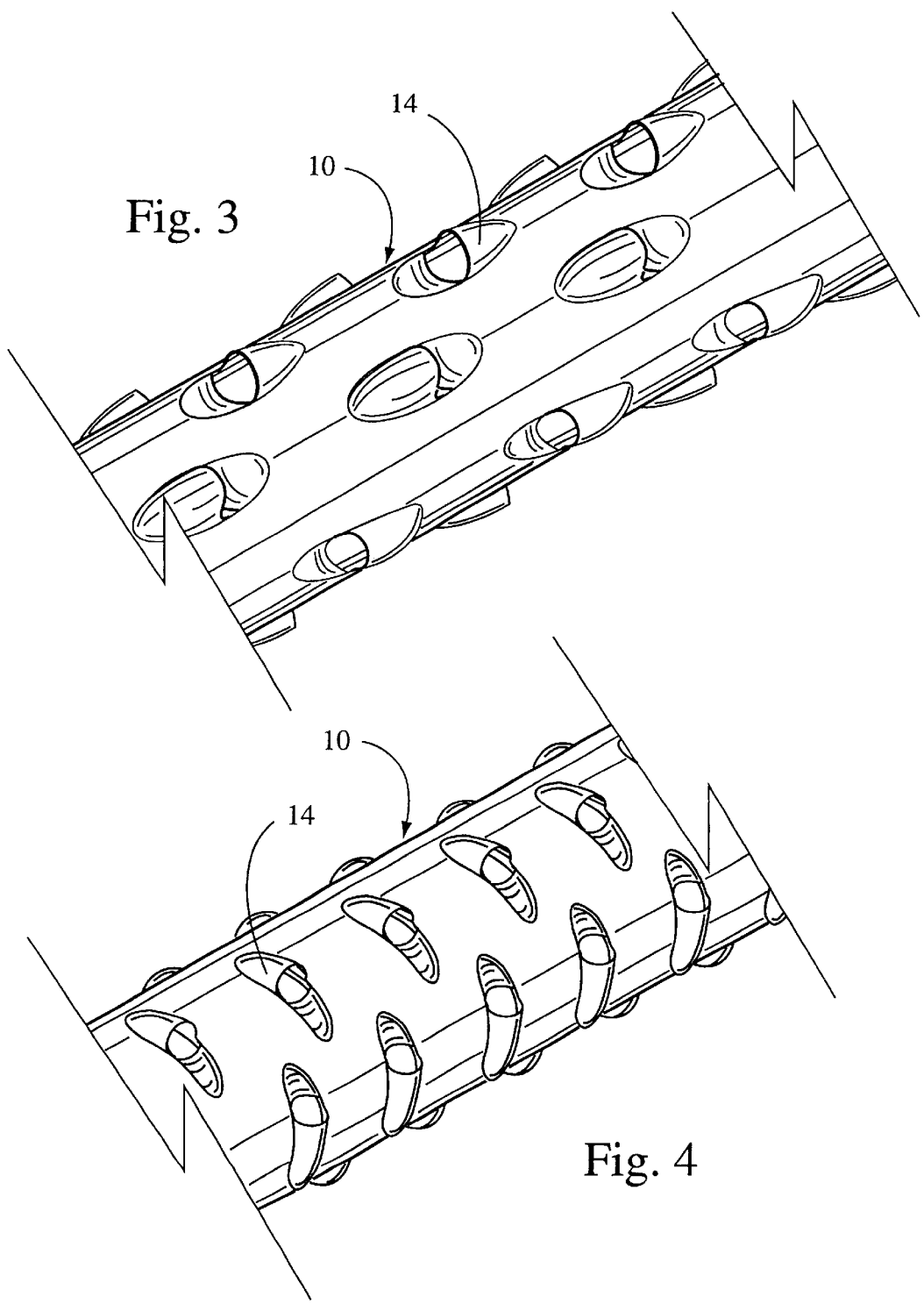

LIPOSUCTION CANNULA WITH ABRADING APERTURES

CROSS-REFERENCE TO RELATED APPLICATIONS (Not Applicable)

STATEMENT RE: FEDERALLY SPONSORED RESEARCH/DEVELOPMENT (Not Applicable)

BACKGROUND OF THE INVENTION

This invention relates in general to liposuction devices, and in particular to a liposuction cannula having abrading suction apertures.

Employment of liposuction procedures to remove unwanted fat has developed over the past approximately 20 years. Initially, general anesthesia was an absolute requirement in order to introduce large cannulas into the affected tissue. Typical cannulas were blunt-tipped, and had diameters of 6–10 mm and cross-sectional areas 9–25 times greater than cannulas available today. Common adverse effects included excessive bleeding, prolonged recovery time, and skin disfigurement.

While the above-described devices and technique are still used by some physicians, many dermatologic surgeons now employ a method broadly known as a tumescent technique which eliminates the requirement of general anesthesia. The term "tumescent technique" means delivering a relatively large volume of a very dilute solution of a local anesthetic agent and a vasoconstrictor agent to the site of liposuction. Thus, the fat removal site is both anesthetized and vasoconstricted so that minimal pain and minimal bleeding occur during the procedure. Concurrently, a small open-tip cannula, generally having a diameter of up to about 2 mm to 3 mm and referred to as a "cannula", is employed for travel through a small incision and positioning at the site of fat removal. Typically, the prior cannula has an open proximal end attachable to a vacuum source to thereby draw lipid substrate through one to three openings at the tip of the cannula and thereafter proximally to the vacuum source. Typically, the cannula is introduced into the fat layer and axially reciprocated to abrade the fat from the tissue and subsequently allow the fat to be aspirated from the patient via suction.

Although the advances described above have greatly reduced the trauma involved in liposuction procedures, a need still exists for a system and method that aids in completing the liposuction procedure more quickly and with less trauma to the patient.

BRIEF SUMMARY OF THE INVENTION

The present invention is directed to a liposuction cannula having a plurality of abrading members and a method of using a cannula with a plurality of abrading members. The liposuction cannula comprises: a hand-holdable housing having a cavity; a cannular tube having a distal end and a proximal end, the proximal end of the cannular tube being insertable within the cavity; and a plurality of abrading suction apertures about the cannular tube distal end.

In accordance with other aspects of the invention, the abrading suction apertures are arranged axially about the distal end of the cannula. Alternatively, the abrading suction apertures are arranged radially about the distal end of the cannula. As yet another alternative, the abrading suction apertures are arranged angularly about the distal end of the cannula.

In accordance with further aspects of the invention, a method of performing liposuction at an adipose tissue site comprises: providing to the tissue site a tumescent quantity of a solution comprising a clinically effective dosage of a local anesthetic and a vasoconstrictor; providing a liposuction cannula, the liposuction cannula having a distal end and a proximal end, the distal end of the cannula having a plurality of abrading suction apertures; placing the liposuction cannula within the adipose tissue site and attaching its proximal end to a vacuum source; and activating the vacuum source while longitudinally moving the cannula forward and backward within the tissue site.

BRIEF DESCRIPTION OF THE DRAWINGS

These as well as other features of the present invention will become more apparent upon reference to the drawings wherein:

FIG. 3 shows an axial arrangement of the abrading suction apertures of the cannula shown in FIG. 2;

FIG. 4 shows a radial arrangement of the abrading suction apertures of the cannula shown in FIG. 2;

DETAILED DESCRIPTION OF THE INVENTION

Figure 1:
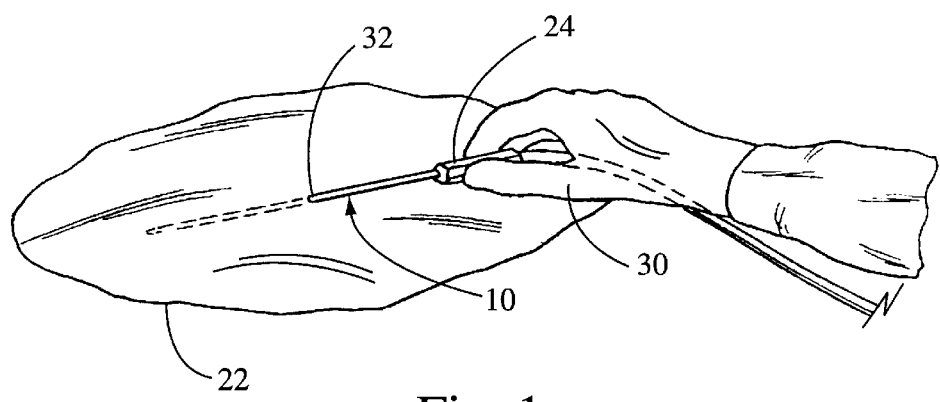
FIG. 1 is a perspective view of a cannula inserted within tissue containing lipid substrate.
Figure 2:
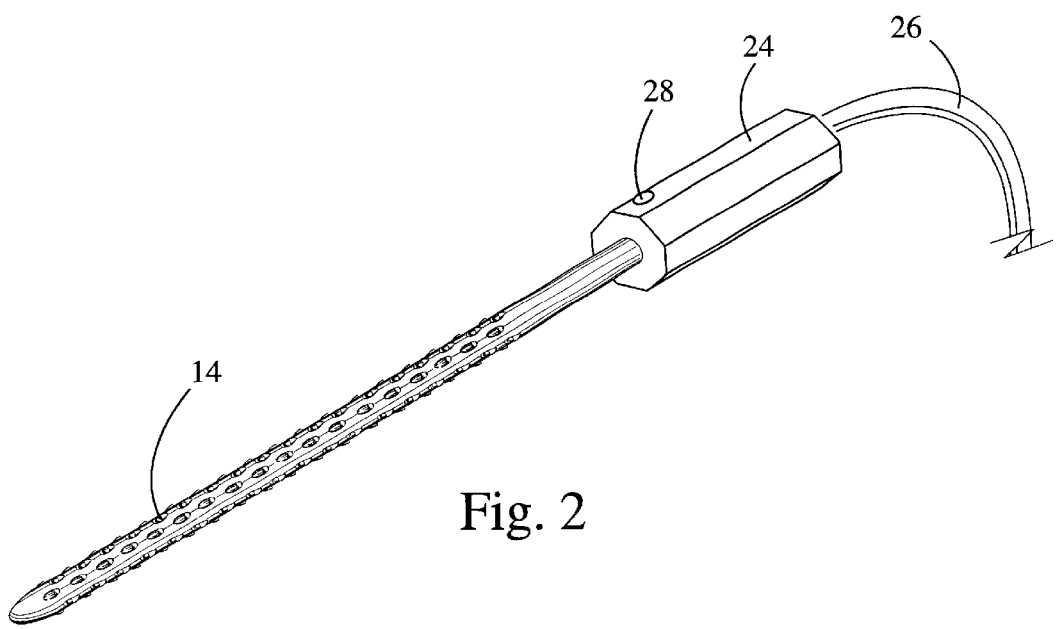
FIG. 2 is a perspective view of the cannula of FIG. 1 attached to a vacuum source.

FIGS. 1 and 2 illustrate a cannula 10 and the use thereof within adipose tissue 22. In particular, the cannula 10 is attached to a handle 24 which is attached to tubing 26 functioning as a vacuum source attached at its other end to a vacuum pump (not shown). The handle 24 may have a conventional thumb-controlled hole 28 such that vacuum is maintained when a user's thumb 30 covers the hole 28 and disappears when the thumb 30 is lifted. The cannula 10 is introduced into tissue 22 to thereby remove lipid substrate.

Figure 5:
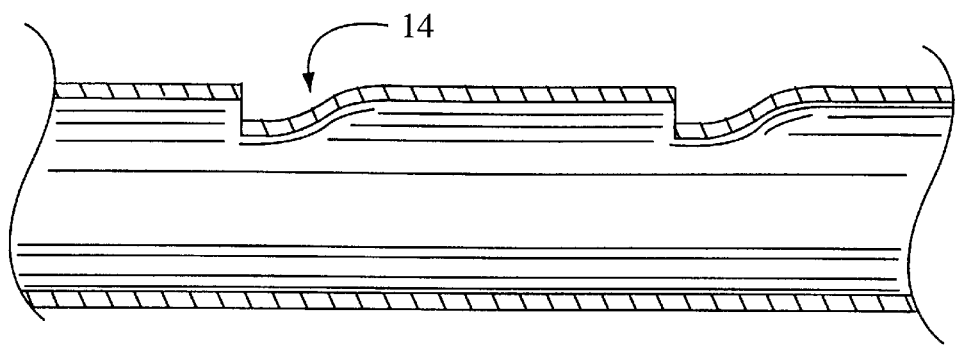
FIG. 5 shows a cross section view of a second embodiment of a cannula having abrading suction apertures comprising a hole and a trailing edge.
Figure 6:
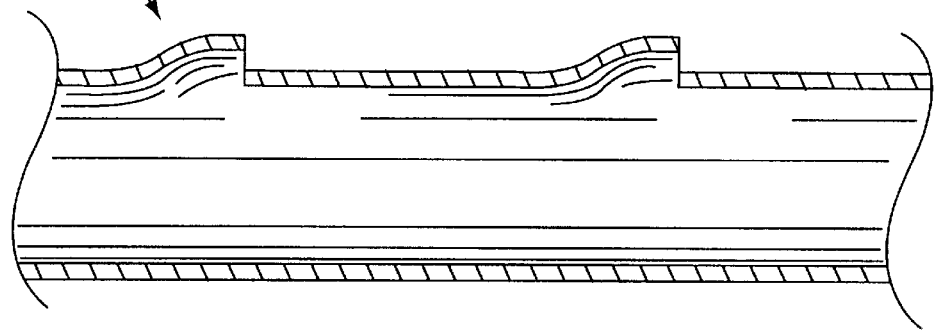
FIG. 6 shows a cross section view of a third embodiment of a cannula having abrading suction apertures comprising a leading edge and a hole.
Figure 7:
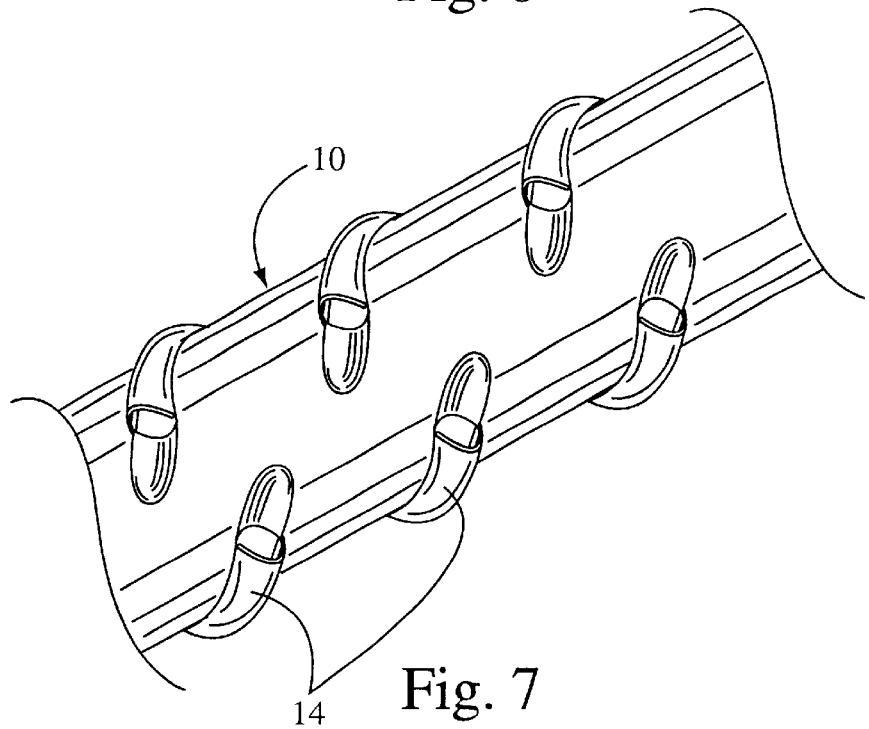
FIG. 7 shows an angular arrangement of the abrading suction apertures of the cannula shown in FIG. 2.

Cannula 10 of the present invention includes a plurality of abrading suction apertures 14 that aid in quickly loosening the tissue in order to minimize trauma to the patient during a liposuction procedure. Preferably, the abrading suction apertures 14 each have a hole, a raised leading edge and a depressed trailing edge as shown in FIGS. 3, 4 and 7. However, it will be appreciated that the abrading suction apertures 14 may each have only a hole and a depressed trailing edge as shown in FIG. 5 or only a hole and a raised leading edge as shown in FIG. 6. It will also be appreciated that a given cannula 10 may use a combination of types of abrading suction apertures 14.

The abrading suction apertures 14 can be arranged in an axial configuration as shown in FIG. 3 or in a radial configuration as shown in FIG. 4. It will be appreciated that virtually any configuration of abrading suction apertures 14 can be used, for example an angular configuration such as that shown in FIG. 7. It will also be appreciated that the orientations of the abrading suction apertures 14 may all be the same, or may alternate in various combinations to alter the rasping effect achieved by the abrading structures 14 of a particular cannula.

Methodology for removing lipid substrate from tissue includes first conventionally providing to the tissue site a tumescent quantity of a solution comprising a clinically effective dosage of a topical anesthetic and a vasoconstrictor. Thereafter, the proximal open end of cannula 10 is attached to the vacuum source tubing 26 through the handle 24. The cannula 10 is then placed within adipose tissue 22 as known in the art through a small incision 32 leading through the skin to the site of the adipose tissue. Once the cannula 10 is in place, the vacuum source is activated and the surgeon grasps the handle 24 as shown in FIG. 1 and controls vacuum delivery through thumb coverage of the thumb hole 28 described above, preferably while moving the cannula forward and backward within the tissue 22 at the site of the adipose tissue. Such movement provides additional rasping force by the abrading suction apertures 14 on the adipose tissue and thereby facilitates adiposyte disassociation from surrounding fibrous tissue. Adipose tissue enters the interior of the cannula tube through the apertures 14 for final removal. Multiple sites are treated through multiple small incisions as would be recognized in the art.

While an illustrative and presently preferred embodiment of the invention has been described in detail herein, it is to be understood that the inventive concepts may be otherwise variously embodied and employed and that the appended claims are intended to be construed to include such variations except insofar as limited by the prior art.

What is claimed is:

1. A liposuction cannula comprising:
   a) a hand holdable housing having a cavity;
   b) a cannular tube having a distal end and a proximal end, the proximal end of the cannular tube being insertable within the cavity; and
   c) a plurality of abrading suction apertures about the cannular tube distal end, at least a portion of the periphery of each of the abrading suction apertures being raised.

2. The liposuction cannula of claim 1, wherein the abrading suction apertures are arranged axially about the distal end of the cannular tube.

3. The liposuction cannula of claim 1, wherein the abrading suction apertures comprise:
   a) a hole;
   b) a raised leading edge; and
   c) a depressed trailing edge.

4. The liposuction cannula of claim 1, wherein the abrading suction apertures comprise:
   a) a hole; and
   b) leading edge.

5. The liposuction cannula of claim 1, wherein the abrading suction apertures comprise:
   a) a hole; and
   b) a depressed trailing edge.

6. A liposuction cannula comprising:
   a) a hand-holdable housing having a cavity;
   b) a cannular tube having a distal end and a proximal end, the proximal end of the cannular tube being insertable within the cavity; and
   c) a plurality of abrading suction apertures about the cannular tube distal end, each of the abrading suction apertures comprising a hole; a raised leading edge; and a depressed trailing edge.

7. The liposuction cannula of claim 6, wherein the abrading suction apertures are arranged axially about the distal end of the cannular tube.

8. A liposuction cannula comprising:
   a) a hand-holdable housing having a cavity;
   b) a cannular tube having a distal end and a proximal end, the proximal end of the cannular tube being insertable within the cavity; and
   c) a plurality of abrading suction apertures about the cannular tube distal end, each of the abrading suction apertures comprising a hole and a raised leading edge.

9. The liposuction cannula of claim 8, wherein the abrading suction apertures are arranged axially about the distal end of the cannular tube.

10. A liposuction cannula comprising:
    a) a hand-holdable housing having a cavity;
    b) a cannular tube having a distal end and a proximal end, the proximal end of the cannular tube being insertable within the cavity; and
    c) a plurality of abrading suction apertures about the cannular tube distal end, each of the abrading suction apertures comprising a hole and a depressed trailing edge.

11. The liposuction cannula of claim 8, wherein the abrading suction apertures are arranged axially about the distal end of the cannular tube.

* * * * *